US 10,194,851 B2

(12) United States Patent
Fletcher et al.

(10) Patent No.: US 10,194,851 B2
(45) Date of Patent: Feb. 5, 2019

(54) BLOOD SAMPLING TRANSFER DEVICE AND BLOOD SEPARATION AND TESTING SYSTEM

(71) Applicant: Becton, Dickinson and Company, Franklin Lakes, NJ (US)

(72) Inventors: Gary D. Fletcher, Sparta, NJ (US); Bradley M. Wilkinson, North Haledon, NJ (US); C. Mark Newby, Tuxedo, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 14/251,710

(22) Filed: Apr. 14, 2014

(65) Prior Publication Data

US 2014/0308166 A1 Oct. 16, 2014

Related U.S. Application Data

(60) Provisional application No. 61/811,918, filed on Apr. 15, 2013.

(51) Int. Cl.
  *A61B 5/15* (2006.01)
  *A61M 1/34* (2006.01)
  (Continued)

(52) U.S. Cl.
  CPC ...... *A61B 5/150213* (2013.01); *A61B 5/1411* (2013.01); *A61B 5/151* (2013.01);
  (Continued)

(58) Field of Classification Search
  CPC .......... A61B 5/150213; A61B 5/15144; A61B 5/150343; A61B 5/150755;
  (Continued)

(56) References Cited

U.S. PATENT DOCUMENTS

| 3,322,114 A | 5/1967 | Portnoy et al. |
| 3,640,393 A | 2/1972 | Hurtig |

(Continued)

FOREIGN PATENT DOCUMENTS

| CN | 1382966 A | 12/2002 |
| CN | 1993079 A | 7/2007 |

(Continued)

OTHER PUBLICATIONS

Membrane Separation Technology for Research and Quality Control, Sartorius AG, Separation Technology, Laboratory Filtration; Mar. 1, 1997.

*Primary Examiner* — Lore R Jarrett
(74) *Attorney, Agent, or Firm* — The Webb Law Firm

(57) ABSTRACT

A blood sampling transfer device that is adapted to receive a blood sample having a cellular portion and a plasma portion is disclosed. The blood sampling transfer device is able to separate the plasma portion from the cellular portion. After separation, the blood sampling transfer device is able to transfer the plasma portion of the blood sample to a point-of-care testing device. The blood sampling transfer device also provides a closed sampling and transfer system that reduces the exposure of a blood sample and provides fast mixing of a blood sample with a sample stabilizer. The blood sampling transfer device is engageable with a blood testing device for closed transfer of a portion of the plasma portion from the blood sampling transfer device to the blood testing device. The blood testing device is adapted to receive the plasma portion to analyze the blood sample and obtain test results.

21 Claims, 12 Drawing Sheets

(51) Int. Cl.
*B01L 3/00* (2006.01)
*B04B 7/08* (2006.01)
*G01N 1/28* (2006.01)
*G01N 1/34* (2006.01)
*G01N 1/40* (2006.01)
*A61B 5/151* (2006.01)
*A61B 5/157* (2006.01)
*G01N 33/49* (2006.01)

(52) U.S. Cl.
CPC ........ *A61B 5/157* (2013.01); *A61B 5/150022* (2013.01); *A61B 5/15101* (2013.01); *A61B 5/15105* (2013.01); *A61B 5/15144* (2013.01); *A61B 5/15198* (2013.01); *A61B 5/150221* (2013.01); *A61B 5/150267* (2013.01); *A61B 5/150305* (2013.01); *A61B 5/150343* (2013.01); *A61B 5/150351* (2013.01); *A61B 5/150412* (2013.01); *A61B 5/150748* (2013.01); *A61B 5/150755* (2013.01); *A61B 5/150778* (2013.01); *A61M 1/34* (2013.01); *B01L 3/502* (2013.01); *B01L 3/5021* (2013.01); *B04B 7/08* (2013.01); *G01N 1/28* (2013.01); *G01N 1/34* (2013.01); *G01N 1/4005* (2013.01); *G01N 1/4077* (2013.01); *G01N 33/491* (2013.01); *A61B 5/150435* (2013.01); *A61B 5/150442* (2013.01); *A61B 5/150969* (2013.01); *B01L 2200/0631* (2013.01); *B01L 2200/10* (2013.01); *B01L 2300/0681* (2013.01); *B01L 2400/0478* (2013.01); *G01N 2001/4016* (2013.01); *G01N 2001/4088* (2013.01)

(58) Field of Classification Search
CPC ........ A61B 5/150778; A61B 5/150748; A61B 5/150412; A61B 5/150305; A61B 5/1411; A61B 5/15101; A61B 5/151; A61B 5/157; A61B 5/15198; A61B 5/15105; A61B 5/150267; A61B 5/150351; A61B 5/150221; A61B 5/150022; A61B 5/150435; A61B 5/150442; A61B 5/150969; G01N 1/4005; G01N 1/4077; G01N 1/34; G01N 33/491; G01N 1/28; G01N 2001/4088; G01N 2001/4016; B01L 3/502; B01L 3/5021; B01L 2400/0478; B01L 2200/0631; B01L 2200/10; B01L 2300/0681; B04B 7/08; A61M 1/34
See application file for complete search history.

(56) References Cited

U.S. PATENT DOCUMENTS

| | | | |
|---|---|---|---|
| 4,511,349 A | 4/1985 | Nielsen et al. | |
| 4,627,445 A | 12/1986 | Garcia et al. | |
| 5,055,203 A | 10/1991 | Columbus | |
| 5,163,442 A | 11/1992 | Ono | |
| 5,219,999 A | 6/1993 | Suzuki et al. | |
| 5,422,018 A | 6/1995 | Saunders et al. | |
| 5,636,640 A | 6/1997 | Staehlin | |
| 5,690,618 A * | 11/1997 | Smith | A61M 5/20 128/DIG. 1 |
| 5,726,026 A | 3/1998 | Wilding et al. | |
| 5,839,715 A | 11/1998 | Leinsing | |
| 5,879,624 A * | 3/1999 | Boehringer | A61M 1/0001 210/645 |
| 5,922,591 A | 7/1999 | Anderson et al. | |
| 6,074,183 A | 6/2000 | Allen et al. | |
| 6,264,619 B1 | 7/2001 | Ferguson | |
| 6,506,167 B1 | 1/2003 | Ishimito et al. | |
| 6,869,405 B2 | 3/2005 | Marsden | |
| 8,075,496 B2 | 12/2011 | Deck et al. | |
| 8,158,410 B2 | 4/2012 | Tang et al. | |
| 2002/0009015 A1 | 1/2002 | Laugharn, Jr. et al. | |
| 2002/0143298 A1 | 10/2002 | Marsden | |
| 2003/0134416 A1 | 7/2003 | Yamanishi et al. | |
| 2003/0232712 A1* | 12/2003 | Dolecek | A61M 1/3696 494/37 |
| 2004/0142463 A1 | 7/2004 | Walker et al. | |
| 2004/0143226 A1 | 7/2004 | Marsden | |
| 2004/0230216 A1 | 11/2004 | Levaughn et al. | |
| 2005/0069459 A1 | 3/2005 | Ahn et al. | |
| 2005/0214927 A1 | 9/2005 | Haley | |
| 2006/0029923 A1 | 2/2006 | Togawa et al. | |
| 2006/0127277 A1* | 6/2006 | Numajiri | G01N 35/08 422/65 |
| 2006/0240964 A1 | 10/2006 | Lolachi et al. | |
| 2007/0031283 A1 | 2/2007 | Davis et al. | |
| 2007/0160503 A1 | 7/2007 | Sethu et al. | |
| 2008/0135502 A1 | 6/2008 | Pyo et al. | |
| 2008/0240990 A1 | 10/2008 | Flaherty | |
| 2009/0004060 A1 | 1/2009 | Omuro et al. | |
| 2009/0136982 A1 | 5/2009 | Tang et al. | |
| 2009/0181411 A1 | 7/2009 | Battrell et al. | |
| 2009/0204026 A1 | 8/2009 | Crawford et al. | |
| 2010/0089815 A1 | 4/2010 | Zhang et al. | |
| 2010/0093551 A1 | 4/2010 | Montagu | |
| 2010/0198108 A1 | 8/2010 | Alden | |
| 2010/0241031 A1 | 9/2010 | Lai | |
| 2011/0124130 A1 | 5/2011 | Wagner et al. | |
| 2011/0124984 A1 | 5/2011 | Rostaing | |
| 2012/0152858 A1 | 6/2012 | Yang | |
| 2012/0275955 A1 | 11/2012 | Haghgooie et al. | |
| 2012/0277696 A1 | 11/2012 | Gonzalez-Zugasti et al. | |
| 2012/0277697 A1 | 11/2012 | Haghgooie et al. | |
| 2013/0026085 A1 | 1/2013 | Samsoondar | |
| 2013/0052675 A1 | 2/2013 | Karlsson et al. | |
| 2013/0082012 A1 | 4/2013 | Lean et al. | |
| 2013/0086980 A1 | 4/2013 | Gadini et al. | |
| 2013/0175213 A1 | 7/2013 | Dorrer et al. | |
| 2013/0209331 A1 | 8/2013 | Rodenfels et al. | |

FOREIGN PATENT DOCUMENTS

| | | |
|---|---|---|
| CN | 101102847 A | 1/2008 |
| CN | 101332320 A | 12/2008 |
| CN | 102764133 A | 11/2012 |
| DE | 202008010918 U1 | 1/2009 |
| EP | 0376168 A2 | 7/1990 |
| EP | 0747105 A2 | 12/1996 |
| EP | 1096254 A2 | 5/2001 |
| EP | 1106065 A2 | 6/2001 |
| EP | 1477804 A1 | 11/2004 |
| EP | 1602329 A1 | 12/2005 |
| EP | 1627651 A2 | 2/2006 |
| EP | 2264453 A1 | 12/2010 |
| EP | 2413138 A2 | 2/2012 |
| FR | 2929135 A1 | 10/2009 |
| FR | 2977808 A1 | 1/2013 |
| JP | 275332 A | 3/1990 |
| JP | 200074908 A | 3/2000 |
| JP | 200319126 A | 1/2003 |
| JP | 2004361419 A | 12/2004 |
| JP | 2010237050 A | 10/2010 |
| JP | 2010146123 A1 | 12/2010 |
| JP | 2012530256 A | 11/2012 |
| WO | 9309710 A1 | 5/1993 |
| WO | 2005018710 A2 | 3/2005 |
| WO | 2006047831 A1 | 5/2006 |
| WO | 2007002579 A2 | 1/2007 |
| WO | 2009123592 A1 | 10/2009 |
| WO | 2011040874 A1 | 4/2011 |
| WO | 2012121686 A1 | 9/2012 |

* cited by examiner

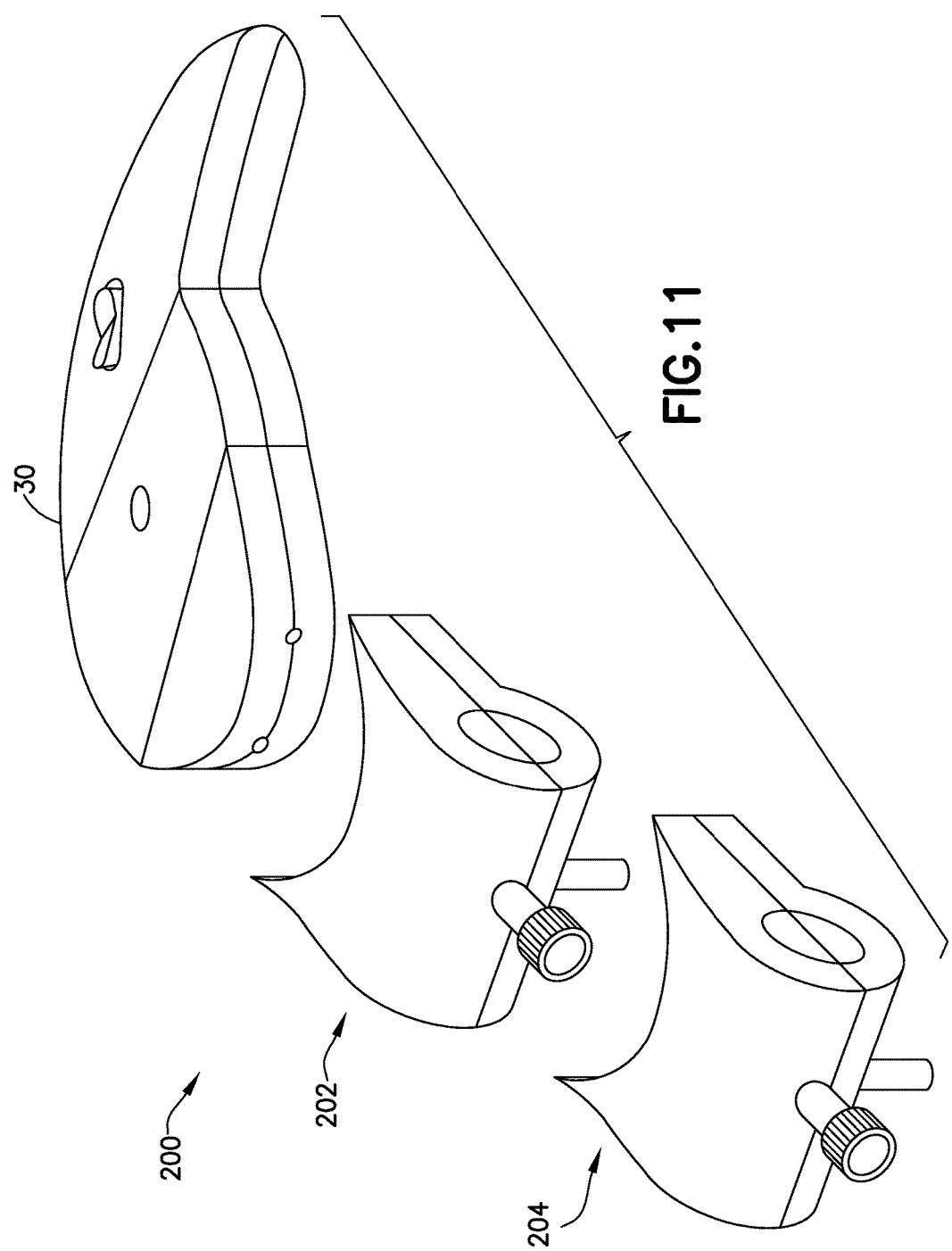

BLOOD SAMPLING TRANSFER DEVICE AND BLOOD SEPARATION AND TESTING SYSTEM

CROSS REFERENCE TO RELATED APPLICATION

The present application claims priority to U.S. Provisional Application No. 61/811,918, filed Apr. 15, 2013, entitled "Medical Device for Collection of a Biological Sample", the entire disclosure of which is hereby incorporated by reference in its entirety.

BACKGROUND OF THE INVENTION

1. Field of the Disclosure

The present disclosure relates generally to devices, assemblies, and systems adapted for use with vascular access devices. More particularly, the present disclosure relates to devices, assemblies, and systems adapted for collecting biological samples for use in point-of-care testing.

2. Description of the Related Art

Blood sampling is a common health care procedure involving the withdrawal of at least a drop of blood from a patient. Blood samples are commonly taken from hospitalized, homecare, and emergency room patients either by finger stick, heel stick, or venipuncture. Blood samples may also be taken from patients by venous or arterial lines. Once collected, blood samples may be analyzed to obtain medically useful information including chemical composition, hematology, or coagulation, for example.

Blood tests determine the physiological and biochemical states of the patient, such as disease, mineral content, drug effectiveness, and organ function. Blood tests may be performed in a clinical laboratory or at the point-of-care near the patient. One example of point-of-care blood testing is the routine testing of a patient's blood glucose levels which involves the extraction of blood via a finger stick and the mechanical collection of blood into a diagnostic cartridge. Thereafter, the diagnostic cartridge analyzes the blood sample and provides the clinician a reading of the patient's blood glucose level. Other devices are available which analyze blood gas electrolyte levels, lithium levels, and ionized calcium levels. Some other point-of-care devices identify markers for acute coronary syndrome (ACS) and deep vein thrombosis/pulmonary embolism (DVT/PE).

Despite the rapid advancement in point-of-care testing and diagnostics, blood sampling techniques have remained relatively unchanged. Blood samples are frequently drawn using hypodermic needles or vacuum tubes attached to a proximal end of a needle or a catheter assembly. In some instances, clinicians collect blood from a catheter assembly using a needle and syringe that is inserted into the catheter to withdraw blood from a patient through the inserted catheter. These procedures utilize needles and vacuum tubes as intermediate devices from which the collected blood sample is typically withdrawn prior to testing. These processes are thus device intensive, utilizing multiple devices in the process of obtaining, preparing, and testing blood samples. Each additional device increases the time and cost of the testing process.

Point-of-care testing devices allow for a blood sample to be tested without needing to send the blood sample to a lab for analysis. Thus, it is desirable to create a device that provides an easy, safe, reproducible, and accurate process with a point-of-care testing system.

SUMMARY OF THE INVENTION

The present disclosure provides a biological fluid sampling transfer device, such as a blood sampling transfer device, that is adapted to receive a blood sample having a cellular portion and a plasma portion. After collecting the blood sample, the blood sampling transfer device is able to separate the plasma portion from the cellular portion. After separation, the blood sampling transfer device is able to transfer the plasma portion of the blood sample to a point-of-care testing device. The blood sampling transfer device of the present disclosure also provides a closed sampling and transfer system that reduces the exposure of a blood sample and provides fast mixing of a blood sample with a sample stabilizer. The sample stabilizer, can be an anticoagulant, or a substance designed to preserve a specific element within the blood such as, for example, RNA, protein analyte, or other element. The blood sampling transfer device is engageable with a blood testing device for closed transfer of a portion of the plasma portion from the blood sampling transfer device to the blood testing device. The blood testing device is adapted to receive the plasma portion to analyze the blood sample and obtain test results.

Some of the advantages of the blood sampling transfer device and the blood separation and testing system of the present disclosure over prior systems are that it is a closed system which reduces blood sample exposure, it provides passive and fast mixing of the blood sample with a sample stabilizer, it facilitates separation of the blood sample without transferring the blood sample to a separate device, and it is capable of transferring pure plasma to a point-of-care testing device. The blood sampling transfer device of the present disclosure enables integrated blood collection and plasma creation in a closed system without centrifugation. The clinician may collect and separate the blood sample and then immediately transfer the plasma portion to the point-of-care testing device without further manipulation. This enables collection and transfer of plasma to the point-of-care testing device without exposure to blood. In addition, the blood sampling transfer device of the present disclosure minimizes process time by processing the blood within the blood sampling transfer device and without external machinery. Further, for tests which only require small amounts of blood, it eliminates the waste associated with blood collection and plasma separation with an evacuated tube.

In accordance with an embodiment of the present invention, a blood sampling transfer device adapted to receive a blood sample having a cellular portion and a plasma portion includes a first component having an actuation member; and a second component removably connected to the first component, the second component comprising: an inlet port; a flow channel; an outlet port, the inlet port and the outlet port in fluid communication via the flow channel; a filter disposed within the flow channel between the inlet port and the outlet port; a first chamber defined between the inlet port and the filter; and a transfer chamber defined between the filter and the outlet port, wherein the inlet port is adapted to receive the blood sample upon actuation of the actuation member, and wherein the filter is adapted to trap the cellular portion in the first chamber and allow the plasma portion to pass through the filter and into the transfer chamber.

In one configuration, the first component is a reusable component. In another configuration, the second component is a disposable component. In yet another configuration, the filter comprises a tangential flow filter. In one configuration, the tangential flow filter utilizes a cross-flow filtration to separate the plasma portion from the cellular portion. In another configuration, the blood sampling transfer device includes an acoustic focus element that oscillates the blood sample over the tangential flow filter. In yet another configuration, the inlet port is adapted to receive the blood sample via connection to a blood collection device. In one configuration, the outlet port is adapted for connection to a point-of-care testing device for closed transfer of a portion of the plasma portion from the transfer chamber to the point-of-care testing device. In another configuration, with the outlet port connected to the point-of-care testing device for closed transfer, the plasma portion is transferred from the transfer chamber to the point-of-care testing device upon actuation of the actuation member.

In accordance with another embodiment of the present invention, a biological fluid separation and testing system, such as a blood separation and testing system, for a blood sample having a cellular portion and a plasma portion includes a blood sampling transfer device adapted to receive the blood sample, the blood sampling transfer device comprising: a first component having an actuation member; and a second component removably connected to the first component, the second component comprising: an inlet port; a flow channel; an outlet port, the inlet port and the outlet port in fluid communication via the flow channel; a filter disposed within the flow channel between the inlet port and the outlet port; a first chamber defined between the inlet port and the filter; and a transfer chamber defined between the filter and the outlet port, wherein the inlet port is adapted to receive the blood sample upon actuation of the actuation member, and wherein the filter is adapted to trap the cellular portion in the first chamber and allow the plasma portion to pass through the filter and into the transfer chamber; and a blood testing device having a receiving port adapted to receive the outlet port of the blood sampling transfer device for closed transfer of a portion of the plasma portion from the transfer chamber to the blood testing device.

In one configuration, with the outlet port connected to the blood testing device for closed transfer, the plasma portion is transferred from the transfer chamber to the blood testing device upon actuation of the actuation member. In another configuration, the blood testing device comprises a point-of-care testing device. In yet another configuration, the first component is a reusable component. In one configuration, the second component is a disposable component. In another configuration, the filter comprises a tangential flow filter. In yet another configuration, the tangential flow filter utilizes a cross-flow filtration to separate the plasma portion from the cellular portion. In one configuration, the blood separation and testing system includes an acoustic focus element that oscillates the blood sample over the tangential flow filter. In another configuration, the inlet port is adapted to receive the blood sample via connection to a blood collection device.

In accordance with another embodiment of the present invention, a blood sampling transfer system adapted to receive a blood sample includes a reusable component having an actuation member; a first disposable component removably connectable to the reusable component, the first disposable component having a first inlet port, wherein the first inlet port is adapted to receive the blood sample upon actuation of the actuation member; and a second disposable component removably connectable to the reusable component, the second disposable component having a second inlet port, wherein the second inlet port is adapted to receive the blood sample upon actuation of the actuation member.

In accordance with another embodiment of the present invention, a blood sampling transfer system adapted to receive a blood sample having a cellular portion and a plasma portion includes a reusable component having an actuation member; a first disposable component removably connectable to the reusable component, the first disposable component having a first inlet port, a first flow channel, a first outlet port, the first inlet port and the first outlet port in fluid communication via the first flow channel, a first filter disposed within the first flow channel between the first inlet port and the first outlet port, a first chamber between the first inlet port and the first filter, and a first transfer chamber between the first filter and the first outlet port, wherein the first inlet port is adapted to receive the blood sample upon actuation of the actuation member, and wherein the first filter is adapted to trap the cellular portion in the first chamber and allow the plasma portion to pass through the first filter and into the first transfer chamber; and a second disposable component removably connectable to the reusable component, the second disposable component having a second inlet port, a second flow channel, a second outlet port, the second inlet port and the second outlet port in fluid communication via the second flow channel, a second filter disposed within the second flow channel between the second inlet port and the second outlet port, a second chamber between the second inlet port and the second filter, and a second transfer chamber between the second filter and the second outlet port, wherein the second inlet port is adapted to receive the blood sample upon actuation of the actuation member, and wherein the second filter is adapted to trap the cellular portion in the second chamber and allow the plasma portion to pass through the second filter and into the second transfer chamber.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 11 is an exploded, perspective view of a blood sampling transfer system in accordance with an embodiment of the present invention.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
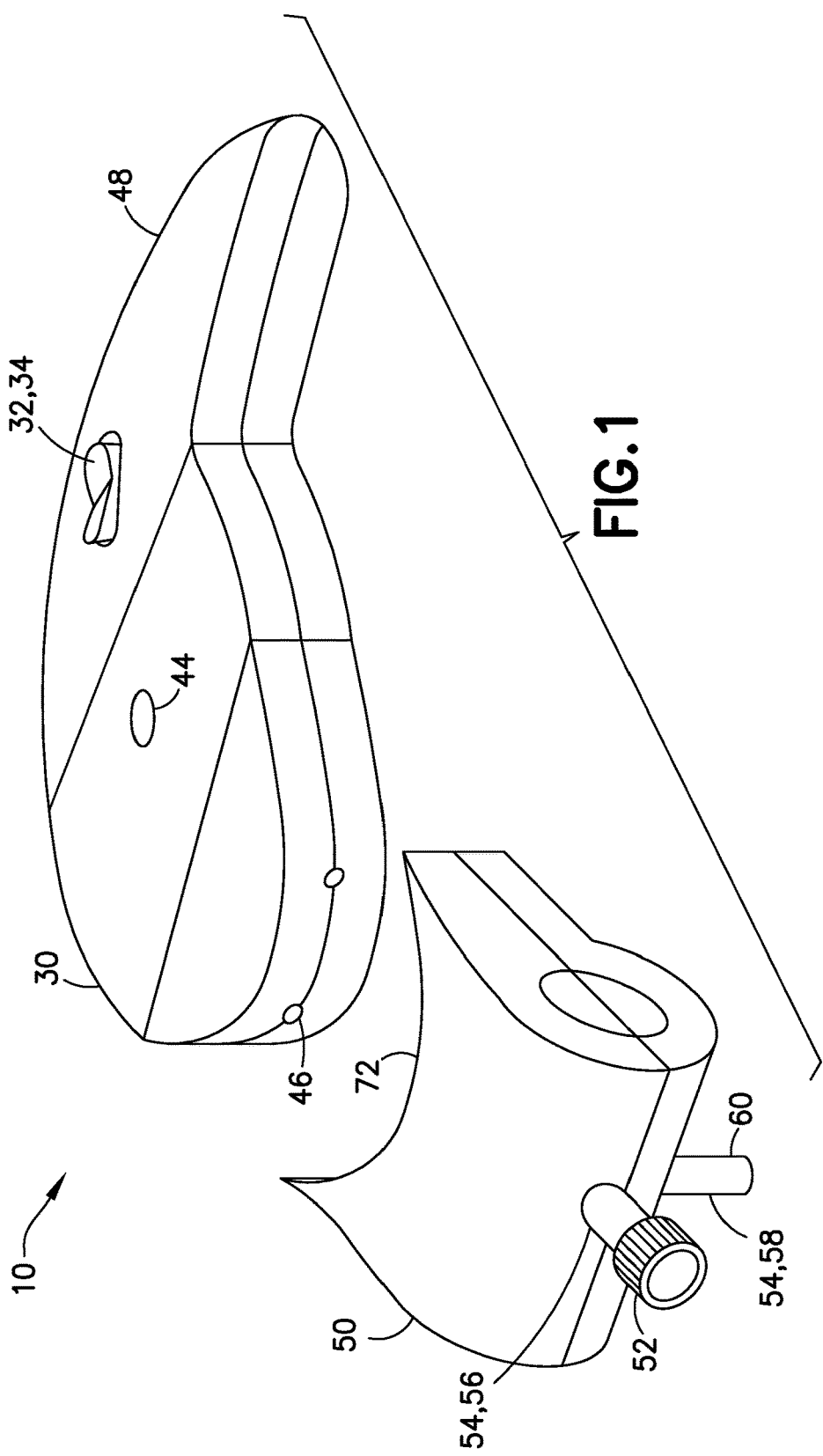
FIG. 1 is an exploded, perspective view of a blood sampling transfer device in accordance with an embodiment of the present invention.
Figure 2:
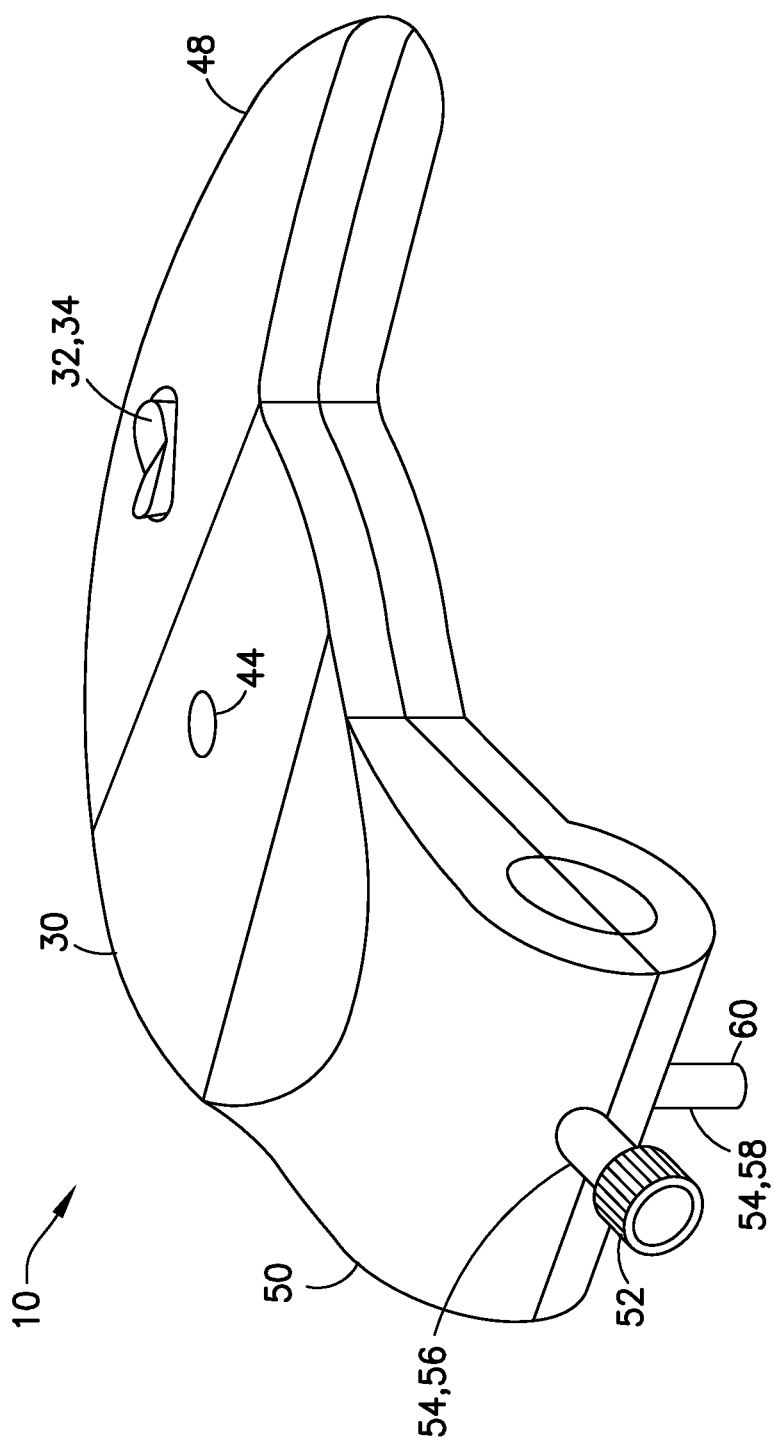
FIG. 2 is an assembled, perspective view of a blood sampling transfer device in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

Various point-of-care testing devices are known in the art. Such point-of-care testing devices include test strips, glass slides, diagnostic cartridges, or other testing devices for testing and analysis. Test strips, glass slides, and diagnostic cartridges are point-of-care testing devices that receive a blood sample and test that blood for one or more physiological and biochemical states. There are many point-of-care devices that use cartridge based architecture to analyze very small amounts of blood at a patient's bedside without the need to send the sample to a lab for analysis. This saves time in getting results over the long run but creates a different set of challenges versus the highly routine lab environment. Examples of such testing cartridges include the i-STAT® testing cartridge from the Abbot group of companies. Testing cartridges such as the i-STAT® cartridges may be used to test for a variety of conditions including the presence of chemicals and electrolytes, hematology, blood gas concentrations, coagulation, or cardiac markers. The results of tests using such cartridges are quickly provided to the clinician.

However, the samples provided to such point-of-care testing cartridges are currently manually collected with an open system and transferred to the point-of-care testing cartridge in a manual manner that often leads to inconsistent results, or failure of the cartridge leading to a repeat of the sample collection and testing process, thereby negating the advantage of the point-of-care testing device. Accordingly, a need exists for a system for collecting and transferring a sample to a point-of-care testing device that provides safer, reproducible, and more accurate results. Accordingly, a point-of-care collecting and transferring system of the present disclosure will be described hereinafter. A system of the present disclosure enhances the reliability of the point-of-care testing device by: 1) incorporating a more closed type of sampling and transfer system; 2) minimizing open exposure of the sample; 3) improving sample quality; 4) improving the overall ease of use; and 5) separating the sample at the point of collection.

FIGS. 1-9 illustrate an exemplary embodiment of the present disclosure. Referring to FIGS. 1-9, a biological fluid sampling transfer device 10, such as a blood sampling transfer device, of the present disclosure is adapted to receive a blood sample 12 having a cellular portion 14 and a plasma portion 16. After collecting the blood sample 12, the blood sampling transfer device 10 is able to separate the plasma portion 16 from the cellular portion 14. After separation, the blood sampling transfer device 10 is able to transfer the plasma portion 16 of the blood sample 12 to a point-of-care testing device. The blood sampling transfer device 10 of the present disclosure also provides a closed sampling and transfer system that reduces the exposure of a blood sample and provides fast mixing of a blood sample with a sample stabilizer.

Figure 5:
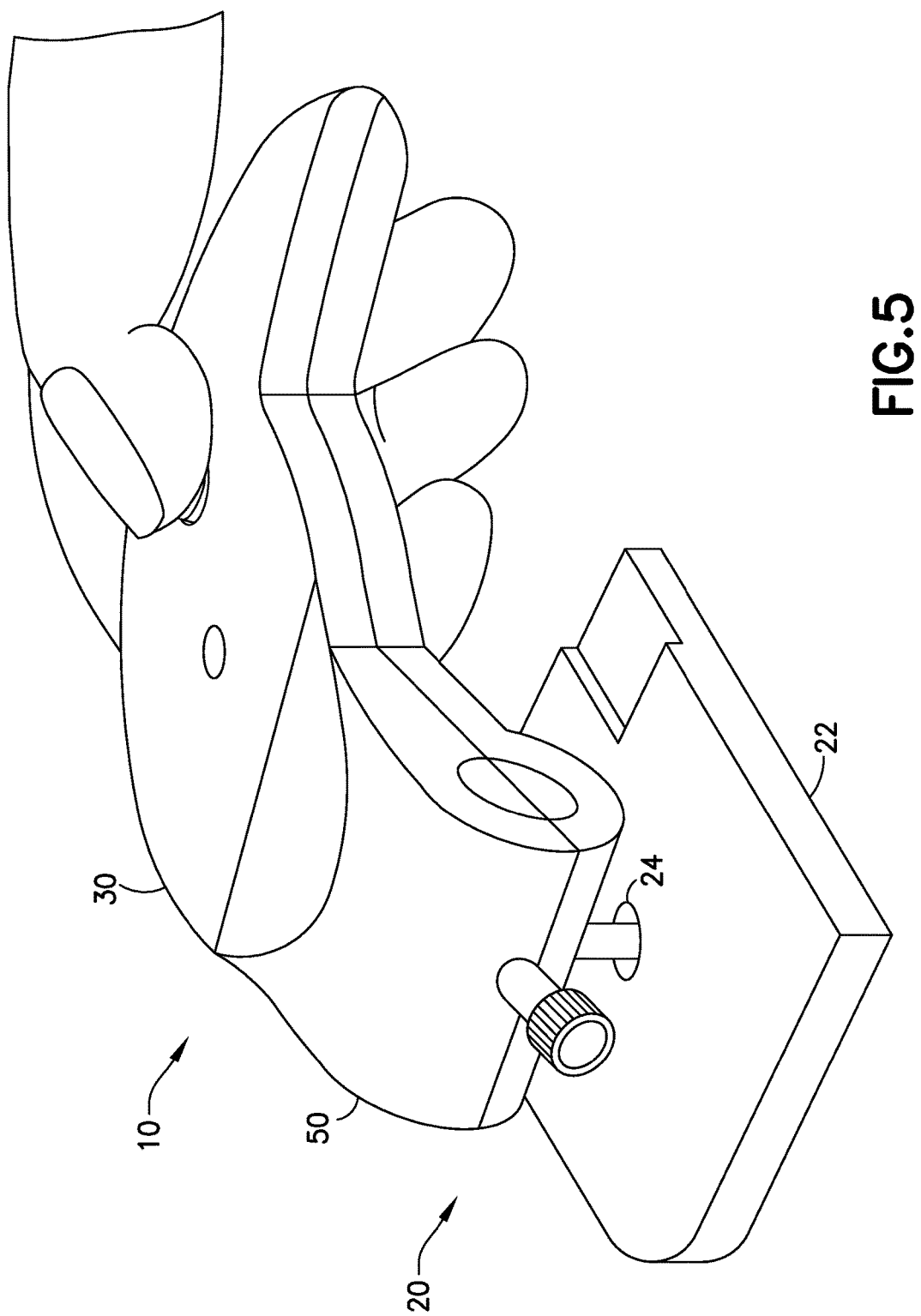
FIG. 5 is a perspective view of a blood sampling transfer device and a point-of-care testing device in accordance with an embodiment of the present invention.
Figure 6:
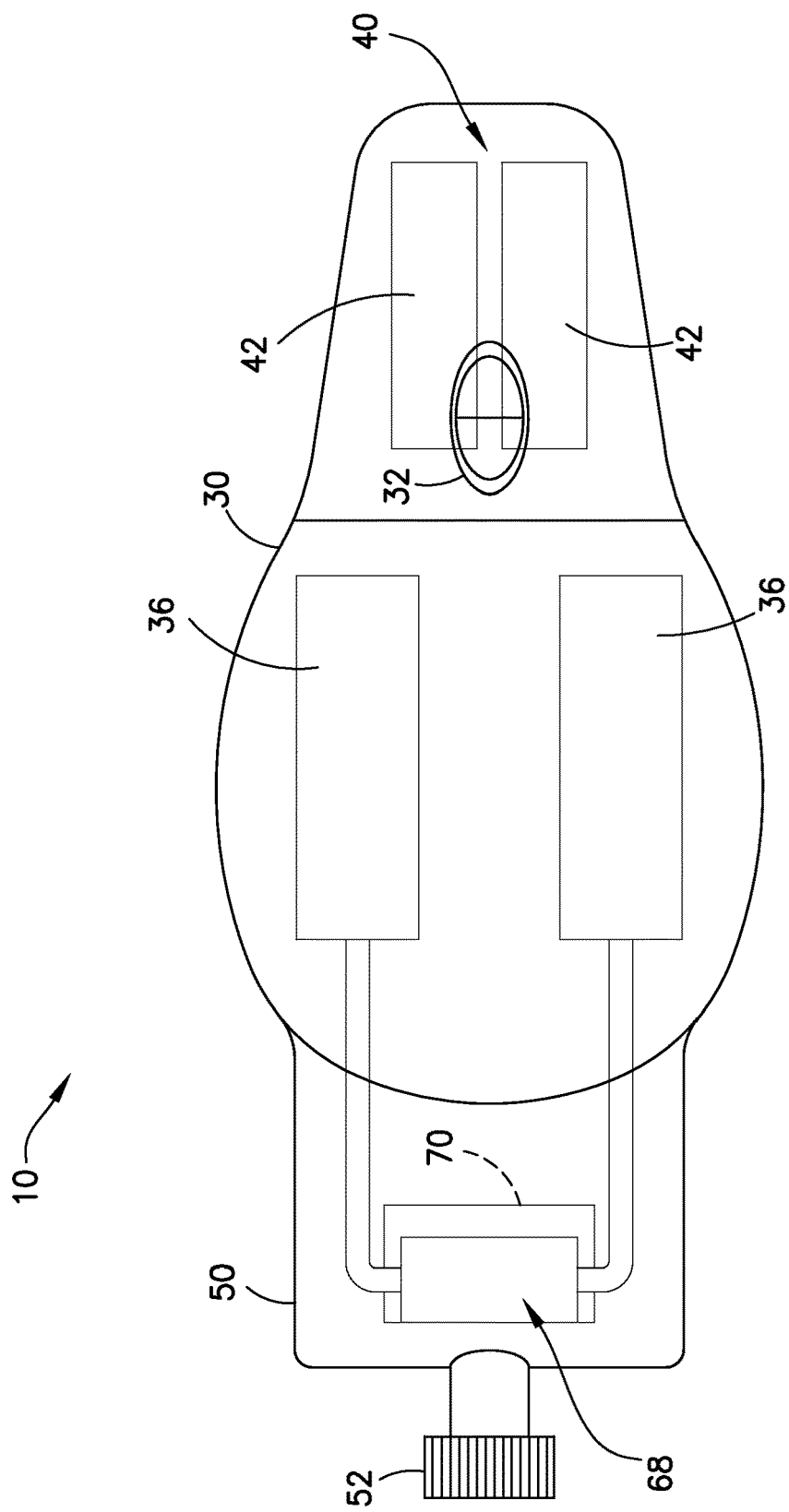
FIG. 6 is a top view of a blood sampling transfer device in accordance with an embodiment of the present invention.
Figure 7:
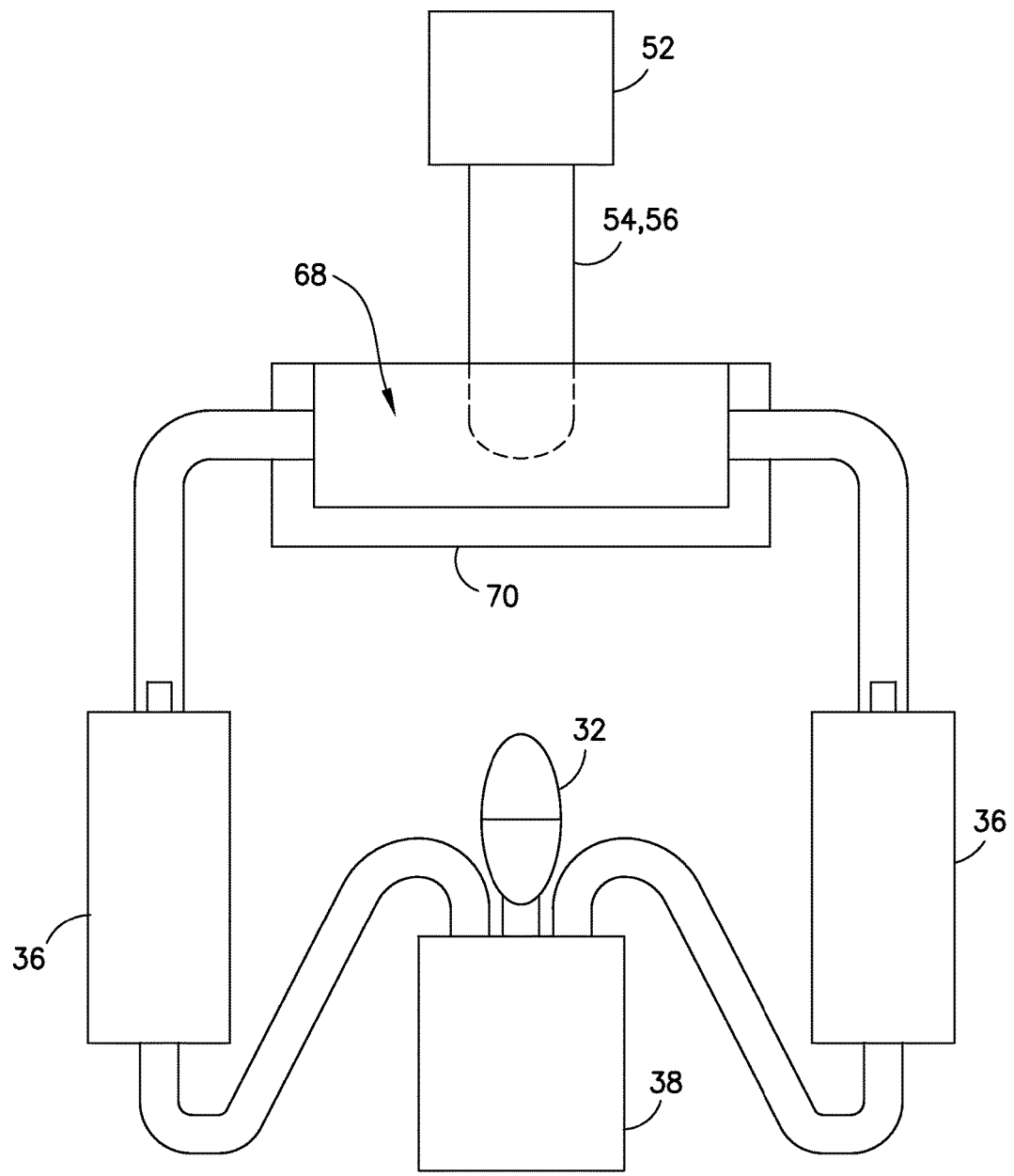
FIG. 7 is a schematic representation of the inside of a first component of a blood sampling transfer device in accordance with an embodiment of the present invention.

FIG. 5 illustrates an exemplary embodiment of the present disclosure. Referring to FIG. 5, a biological fluid separation and testing system 20, such as a blood separation and testing system, of the present disclosure includes a blood sampling transfer device 10 and a blood testing device or point-of-care testing device 22 engageable with the blood sampling transfer device 10 for closed transfer of a portion of the plasma portion 16 (FIG. 8) from the blood sampling transfer device 10 to the blood testing device 22. The blood testing device 22 is adapted to receive the plasma portion 16 to analyze the blood sample and obtain test results.

FIG. 11 illustrates an exemplary embodiment of the present disclosure. Referring to FIG. 11, a blood sampling transfer system 200 of the present disclosure includes a reusable component 30 and a first disposable component 202 that is removably connectable to the reusable component 30 and a second disposable component 204 that is removably connectable to the reusable component 30.

Some of the advantages of the blood sampling transfer device and the blood separation and testing system of the present disclosure over prior systems are that it is a closed system which reduces blood sample exposure, it provides passive and fast mixing of the blood sample with a sample stabilizer, it facilitates separation of the blood sample without transferring the blood sample to a separate device, and it is capable of transferring pure plasma to a point-of-care testing device. The blood sampling transfer device of the present disclosure enables integrated blood collection and plasma creation in a closed system without centrifugation. The clinician may collect and separate the blood sample and then immediately transfer the plasma portion to the point-of-care testing device without further manipulation. This enables collection and transfer of plasma to the point-of-care testing device without exposure to blood. In addition, the blood sampling transfer device of the present disclosure minimizes process time by processing the blood within the blood sampling transfer device and without external machinery. Further, for tests which only require small amounts of blood, it eliminates the waste associated with blood collection and plasma separation with an evacuated tube.

Referring to FIGS. 1-9, a blood sampling transfer device 10 includes a first component or reusable component 30 and a second component or disposable component 50 that is removably connected to the first component 30. The blood sampling transfer device 10 is adapted to receive a blood sample 12 having a cellular portion 14 and a plasma portion 16.

Referring to FIGS. 1-7, the first component 30 generally includes an actuation member 32, a pair of internal miniature pumps 36, a logic control board 38, a power source 40, an indicator element 44, a first securement portion 46, and a handle portion 48. In one embodiment, the actuation member 32 includes a two-way power switch or power button 34. In one embodiment, the power source 40 includes batteries 42. In one embodiment, the indicator element 44 includes a colored LED.

Referring to FIGS. 1-9, the second component 50 generally includes an inlet port 52, a flow channel 54 having an inlet channel 56 and an exit channel 58, an exit port or outlet port 60 in fluid communication with the inlet port 52 via the flow channel 54, a separation chamber 62 having a first chamber 64 and a second chamber or transfer chamber 66, a separation member 68 disposed within the flow channel 54 between the inlet port 52 and the outlet port 60, an acoustic focus element 70, and a second securement portion 72. The first chamber 64 of the separation chamber 62 is defined between the inlet port 52 and the separation member 68. The second chamber 66 of the separation chamber 62 is defined between the separation member 68 and the outlet port 60.

The first component 30 and the second component 50 are removably connectable theretogether such that significant relative movement between the first component 30 and the second component 50 is prevented. In one embodiment, the first component 30 and the second component 50 are removably connectable theretogether via engagement of the first securement portion 46 of the first component 30 with the second securement portion 72 of the second component 50. In other embodiments, similar connection mechanisms may be used. For example, a snap fit engagement mechanism or a friction fit engagement mechanism may be used. The second component 50 of the blood sampling transfer device 10 is adapted to receive a blood sample 12 therein. The blood sample 12 may include a cellular portion 14 and a plasma portion 16.

With the first component 30 and the second component 50 connected, the inlet port 52 is adapted to receive the blood sample upon actuation of the actuation member 32 as discussed in more detail below. With the blood sample received within the blood sampling transfer device 10, the pumps 36 provide a mechanism to oscillate the blood sample back and forth over the filter 68. The pumps 36 are controlled by the logic control board 38. The power source 40 provides power to the actuation member 32.

Figure 3:
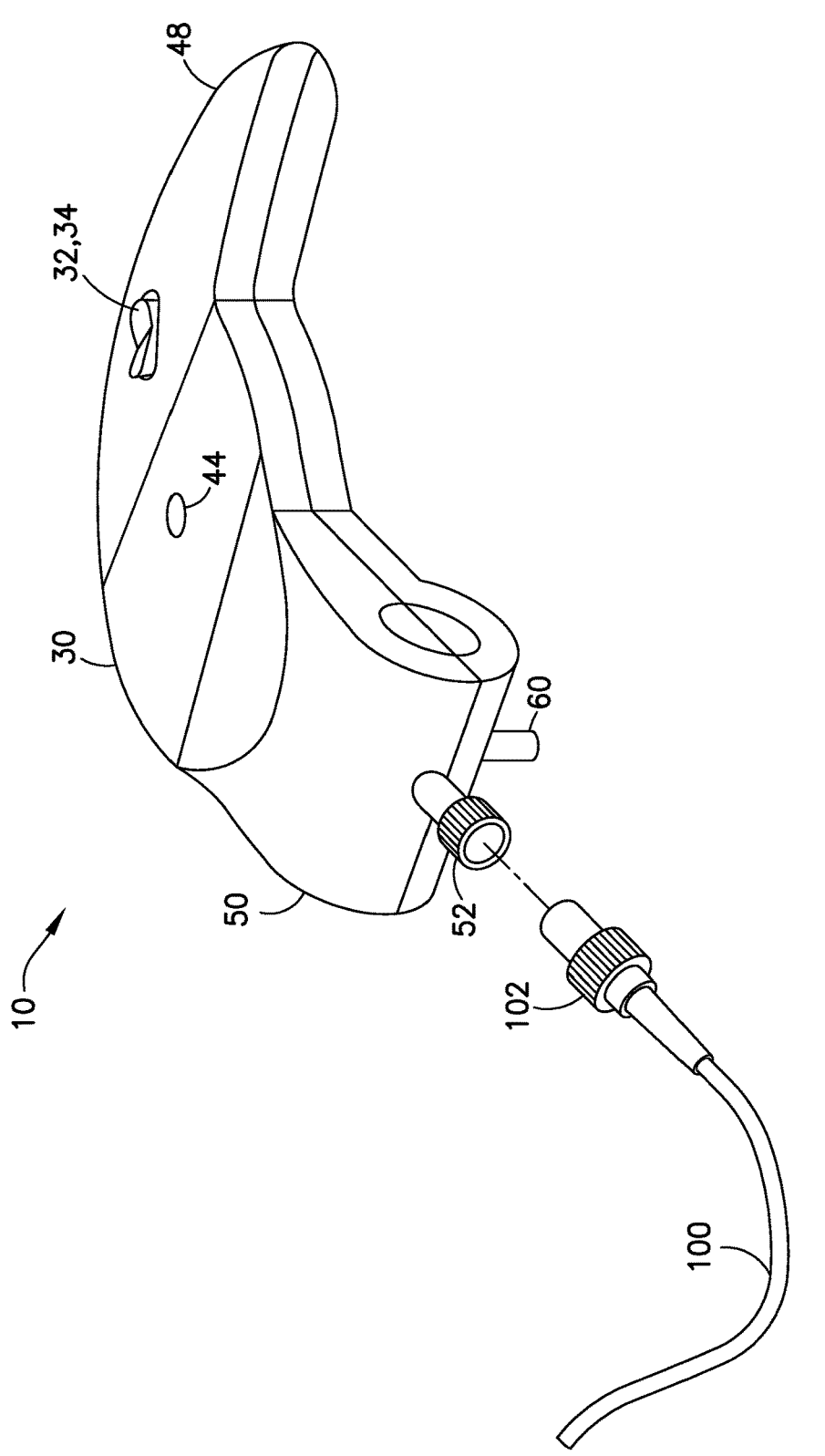
FIG. 3 is a perspective view of a blood sampling transfer device in accordance with an embodiment of the present invention, with a blood collection device.
Figure 4:
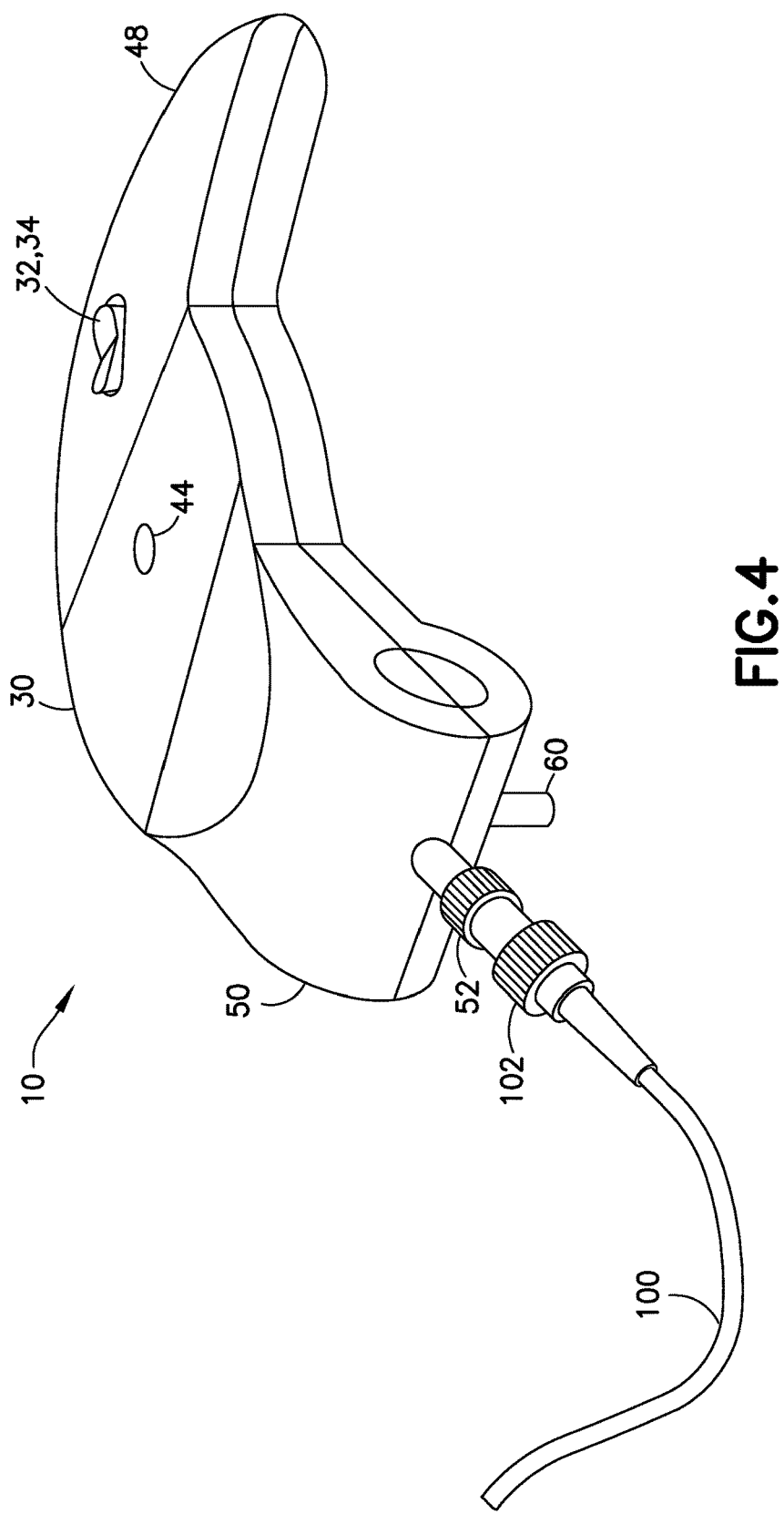
FIG. 4 is a perspective view of a blood sampling transfer device in accordance with an embodiment of the present invention, with a blood collection device attached to the blood sampling transfer device.

Referring to FIGS. 3 and 4, the inlet port 52 of the blood sampling transfer device 10 is adapted to be connected to a blood collection set or blood collection device 100 to allow for the collection of a blood sample 12 into the blood sampling transfer device 10. The inlet port 52 may be sized and adapted for engagement with a separate device, such as a needle assembly or IV connection assembly and, therefore, may include a mechanism for such engagement as is conventionally known. For example, in one embodiment, the inlet port 52 may include a luer lock or luer tip for engagement with an optional separate luer mating component of such a separate device for attachment therewith. For example, referring to FIGS. 3 and 4, the blood collection set 100 may include a luer component 102 for engagement with the inlet port 52 of the blood sampling transfer device 10. In this manner, the inlet port 52 is connectable to the blood collection set 100 for the collection of a blood sample into the blood sampling transfer device 10. In addition, a mechanism for locking engagement between the inlet port 52 and the blood collection set 100 may also be provided. Such luer connections and luer locking mechanisms are well known in the art. The blood collection set 100 may include a needle assembly, an IV connection assembly, a PICC line, an arterial indwelling line, or similar blood collection means.

The inlet port 52 may also include a resealable septum that is transitionable between a closed position and an open position. With the septum in an open position, a blood sample 12 may flow through the inlet port 52 to the first chamber 64 of the separation chamber 62 via the inlet channel 56 of the flow channel 54.

Figure 8:
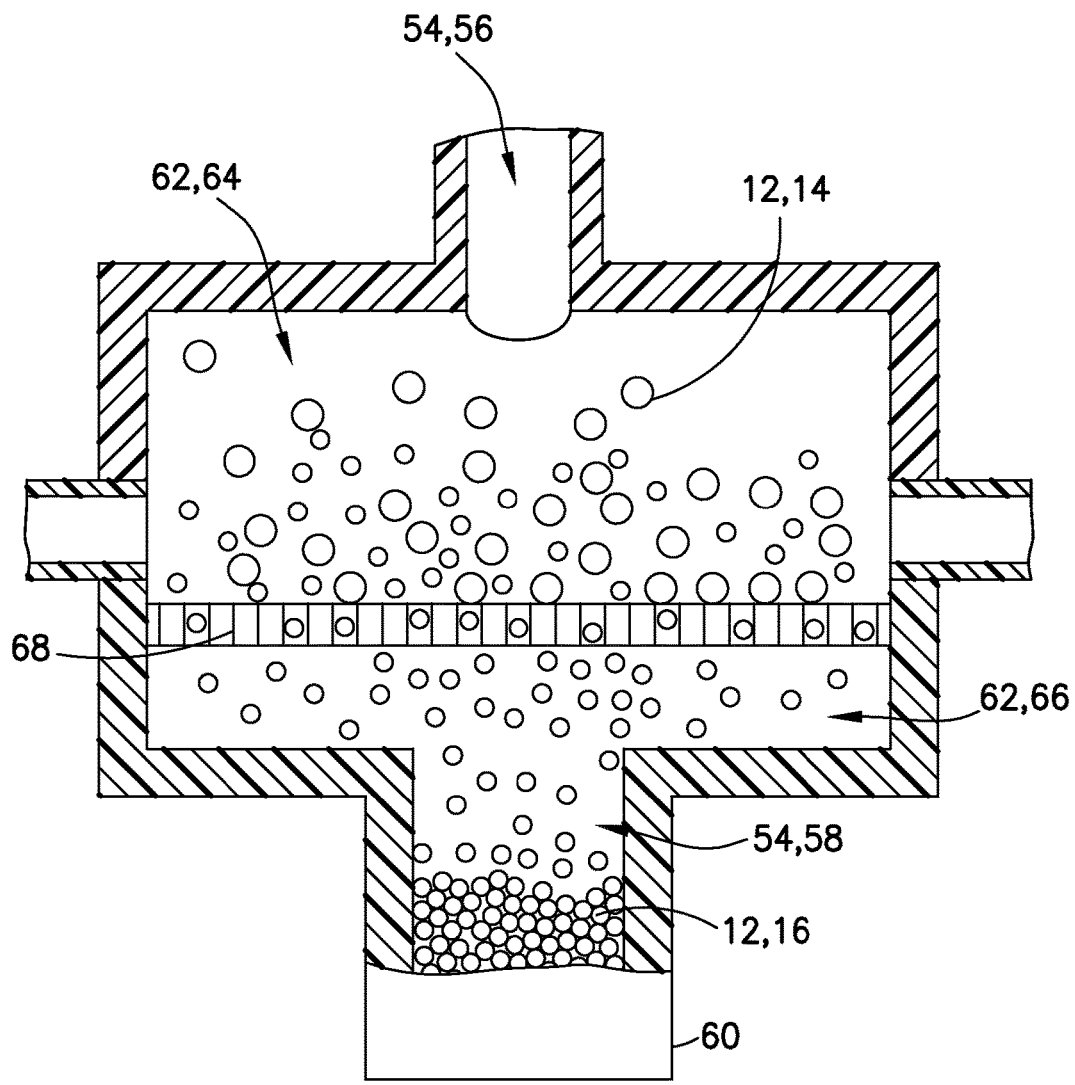
FIG. 8 is a cross-sectional view of a filter of a blood sampling transfer device in accordance with an embodiment of the present invention, with the filter separating a plasma portion of a blood sample from a cellular portion of the blood sample.
Figure 9:
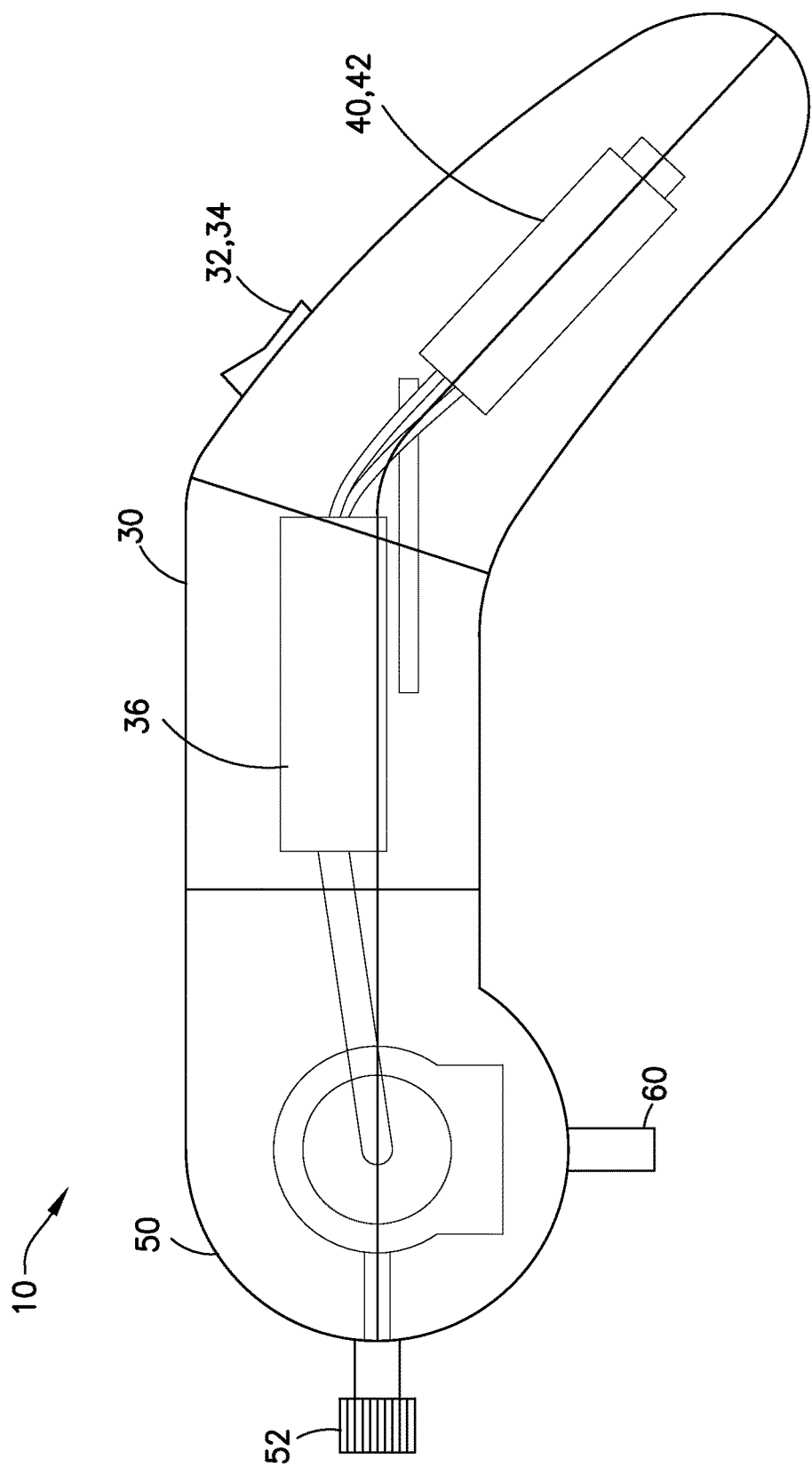
FIG. 9 is a side elevation view of a blood sampling transfer device in accordance with an embodiment of the present invention.

Referring to FIG. 8, the separation chamber 62 is sealed such that a cellular portion 14 of the blood sample 12 is contained within the first chamber 64 of the separation chamber 62 and the plasma portion 16 of the blood sample 12 can exit the first chamber 64 by passing through the filter 68 to the second or transfer chamber 66 as discussed below. Only the plasma portion 16 of the blood sample 12 is able to pass through the filter 68.

The second component 50 of the blood sampling transfer device 10 also may include an acoustic focus element 70 and a valve or septum 86 (FIGS. 12 and 13) at the outlet port 60. The outlet port 60 is adapted for connection to a point-of-care testing device 22 for closed transfer of a portion of the plasma portion 16 from the blood sampling transfer device 10 to the point-of-care testing device 22 via the outlet port 60 as described in more detail below. Referring to FIG. 8, the outlet port 60 is in fluid communication with the second or transfer chamber 66. The valve or septum 86 at the outlet port 60 is transitionable between a closed position and an open position. With the valve or septum 86 in an open position (FIG. 13), the plasma portion 16 of the blood sample 12 may flow through the outlet port 60 to a blood testing device or a point-of-care testing device 22 (FIG. 5).

In one embodiment, the acoustic focus element 70 is disposed within the second component 50 and oscillates the blood sample 12 over the separation member 68 as shown in FIG. 8. The acoustic focus element 70 may focus red blood cells to the center of the separation chamber 62 and the separation member 68 prior to passing through the separation member 68.

In one embodiment, a portion of the flow channel 54 or the inlet port 52 may also include a layer of sample stabilizer. The sample stabilizer can be an anticoagulant, or a substance designed to preserve a specific element within the blood such as, for example, RNA, protein analyte, or other element. In one embodiment, the layer of sample stabilizer may be disposed over the filter 68. In other embodiments, the layer of sample stabilizer may be located anywhere between the inlet port 52 and the filter 68. In this manner, as a blood sample 12 flows through the inlet port 52 and into the first chamber 64 of the separation chamber 62, the blood sampling transfer device 10 provides passive and fast mixing of the blood sample 12 with the sample stabilizer.

The second component 50 of the blood sampling transfer device 10 includes a filter 68 disposed between the first chamber 64 and the second chamber 66 as shown in FIG. 8. The filter 68 is adapted to trap the cellular portion 14 of the blood sample 12 within the first chamber 64 and allow the plasma portion 16 of the blood sample 12 to pass through the filter 68 to the second chamber 66 as shown in FIG. 8. In one embodiment, the filter 68 includes a tangential flow filter. The tangential flow filter utilizes a cross-flow filtration to separate the plasma portion 16 from the cellular portion 14.

In one embodiment, the filter 68 may be either hollow fiber membrane filters commercially available, or flat membrane filters, such as track-etch filters commercially available. Membrane filter pore size and porosity can be chosen to optimize separation of clean (i.e., red blood cell free, white blood cell free, and platelet free) plasma in an efficient manner. In another embodiment, the filter 68 includes a lateral flow membrane. In other embodiments, the filter 68 may comprise any filter that is able to trap the cellular portion 14 of the blood sample 12 within the first chamber 64 and allow the plasma portion 16 of the blood sample 12 to pass through the filter 68 to the second chamber 66.

Referring to FIG. 5, a blood testing device or point-of-care testing device 22 includes a receiving port 24 adapted to receive the outlet port 60 of the blood sampling transfer device 10. The blood testing device 22 is adapted to receive the outlet port 60 of the blood sampling transfer device 10 for closed transfer of a portion of the plasma portion 16 (FIG. 8) from the blood sampling transfer device 10 to the blood testing device 22. The blood testing device 22 is adapted to receive the plasma portion 16 to analyze the blood sample and obtain test results.

As discussed above, the outlet port 60 of the blood sampling transfer device 10 may include a valve or septum 86 that is transitionable between a closed position and an open position. With the valve or septum 86 in an open position (FIG. 13), the plasma portion 16 of the blood sample 12 may flow through the outlet port 60 to a blood testing device or a point-of-care testing device 22 (FIG. 5).

Figure 13:
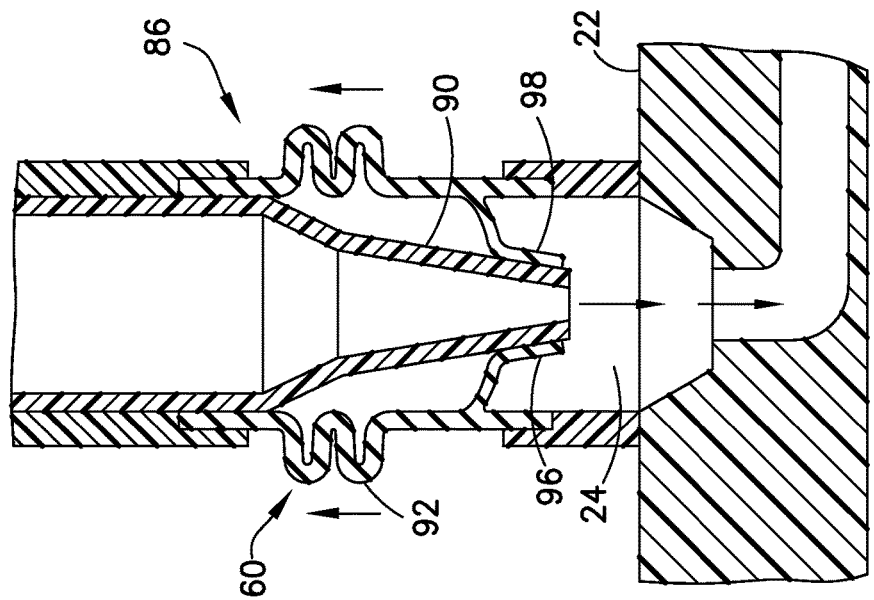
FIG. 13 is a cross-sectional view of a septum of a blood sampling transfer device in accordance with an embodiment of the present invention, with the septum in an open position.
Figure 12:
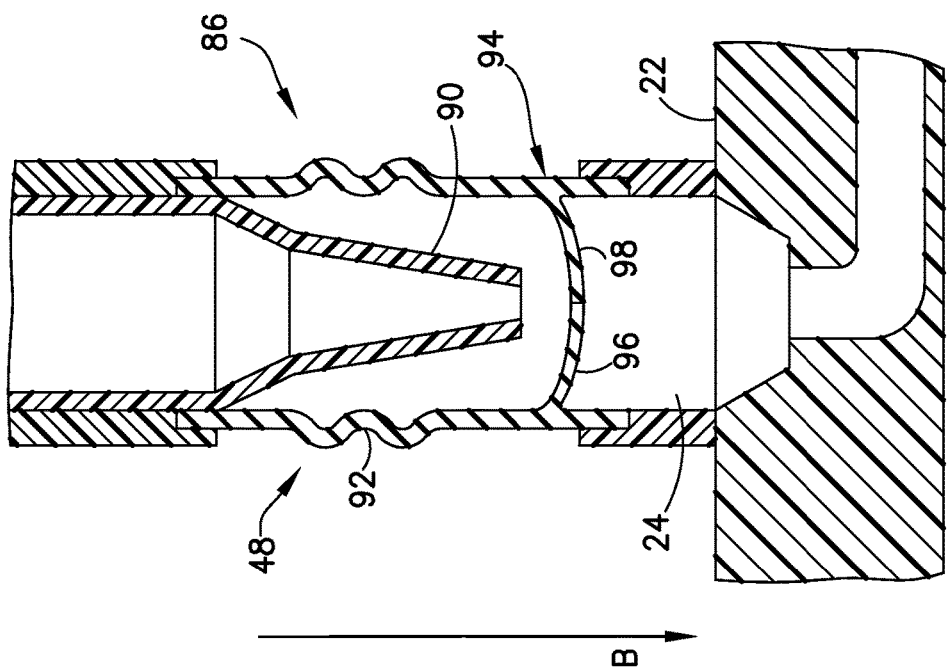
FIG. 12 is a cross-sectional view of a septum of a blood sampling transfer device in accordance with an embodiment of the present invention, with the septum in a closed position.

In one embodiment, referring to FIGS. 12 and 13, the valve 86 may generally include a transfer channel 90, a bellows or deformable wall member 92, and a septum or barrier 94 having a first barrier wall 96 and a second barrier wall 98. Referring to FIG. 12, the valve 86 is in a closed position to prevent the plasma portion 16 of the blood sample 12 from flowing through the outlet port 60. In this manner, the plasma portion 16 is sealed within the blood sampling transfer device 10. Referring to FIG. 13, the valve 86 is in an open position so that the plasma portion 16 of the blood sample 12 may flow through the outlet port 60 to a blood testing device or a point-of-care testing device 22 (FIG. 5).

Referring to FIG. 12, with the plasma portion 16 received within the transfer chamber 66 of the blood sampling transfer device 10 (FIG. 8), the outlet port 60 of the blood sampling transfer device 10 is then positioned over the receiving port 24 of the point-of-care testing device 22. Pushing down in the direction of arrow B compresses the deformable wall member 92 and opens up the first barrier wall 96 and the second barrier wall 98 of the septum 94 as shown in FIG. 12. With the valve 86 in the open position, the plasma portion 16 of the blood sample 12 is allowed to flow through the outlet port 60 and the receiving port 24 to the point-of-care testing device 22 in a closed manner reducing exposure to the clinician and the patient.

The valve 86 of the blood sampling transfer device 10 only opens when the outlet port 60 is pressed upon the receiving port 24 of the point-of-care testing device 22. This releases the isolated plasma portion 16 directly into the receiving port 24 of the point-of-care testing device 22, thus mitigating unnecessary exposure to the patient's blood.

Referring to FIG. 11, a blood sampling transfer system 200 of the present disclosure will now be discussed. The blood sampling transfer system 200 includes a reusable component 30 and a first disposable component 202 that is removably connectable to the reusable component 30 and a second disposable component 204 that is removably connectable to the reusable component 30.

Figure 10:
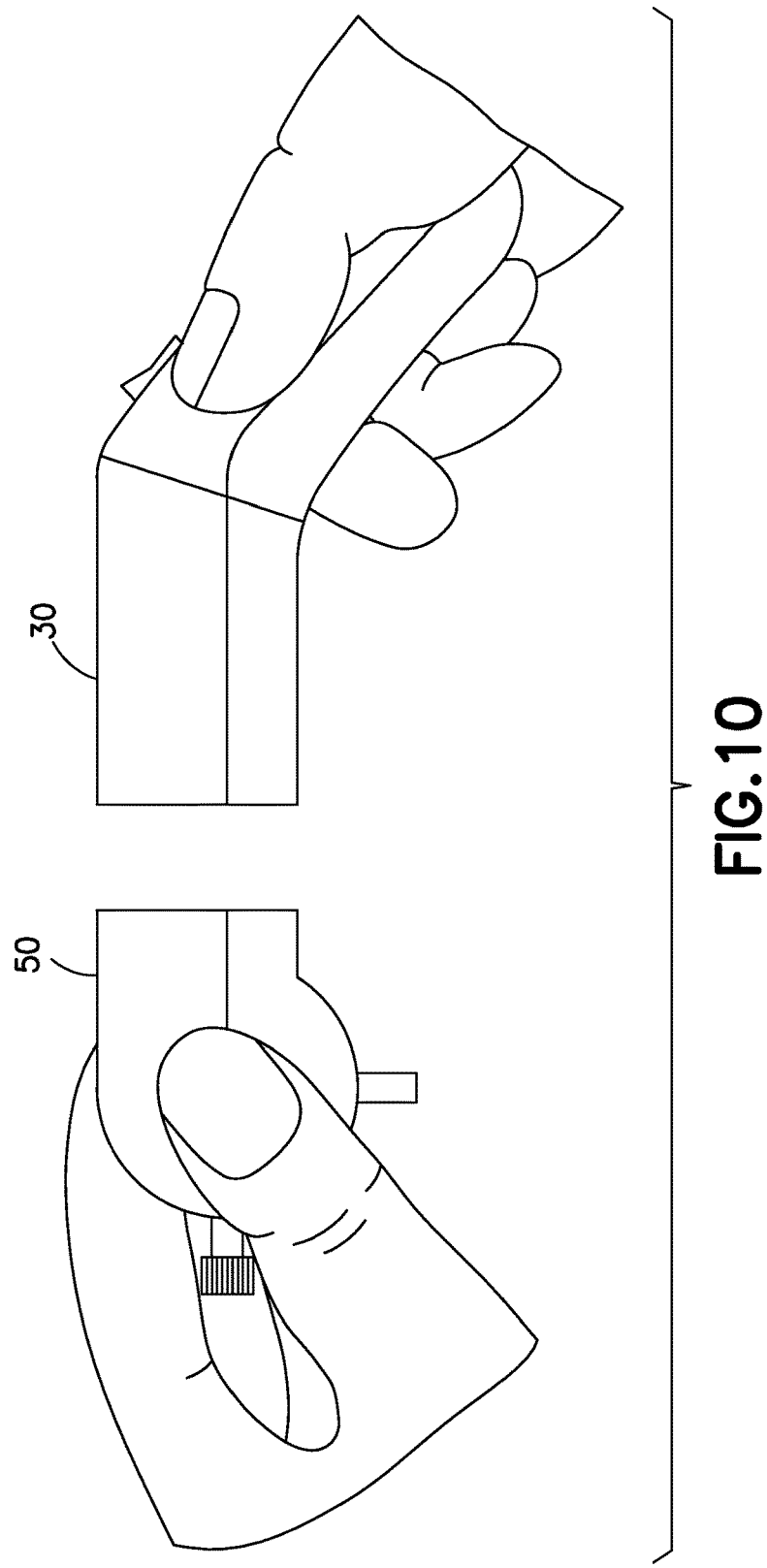
FIG. 10 is a perspective view of a blood sampling transfer device in accordance with an embodiment of the present invention, with a first component being removed from a second component.

As will be described below, after use of a disposable component 50, the disposable component 50 can be removed from the first component 30, as shown in FIG. 10, and the disposable component 50 can be disposed of into a biological hazard container. One advantage of the blood sampling transfer system 200 of the present disclosure is that a plurality of disposable components 50, i.e., a first disposable component 202 and a second disposable component 204, can be used with the reusable component 30. In other embodiments, any number of disposable components can be used with the reusable component 30. In this manner, the reusable component 30 which includes the actuation member 32 can be used repeatedly while the disposable components, including the relevant sharps, can be discarded. Once a disposable component 50 is used, it can be removed from the first component 30, as shown in FIG. 10, and the disposable component 50 can be disposed of into a biological hazard container. When it is desired to use the blood sampling transfer device 10 again, a new and clean disposable component can be selected and used with the reusable component 30.

Referring to FIGS. 1-10, use of a blood sampling transfer device and blood separation and testing system of the present disclosure will now be described. Referring to FIGS. 3 and 4, the inlet port 52 of the blood sampling transfer device 10 is adapted to be connected to a blood collection set 100 to allow for the collection of a blood sample 12 into the blood sampling transfer device 10 as discussed above. Once the blood collection set 100 is connected to a patient, the actuation member 32 of the first component 30 is activated, e.g., the power switch 34 is pushed down, to draw the blood sample into the separation chamber 62 of the second or disposable component 50. As this happens, the blood sample 12 is oscillated back and forth over the filter 68. Also, as the blood sample 12 slowly fills the blood sampling transfer device 10, it is collected and stabilized over a layer of sample stabilizer. Referring to FIG. 8, the plasma portion 16 of the blood sample 12 may then flow through the filter 68 so that the plasma portion 16 is separated from the cellular portion 14. The plasma portion 16 passes through the filter 68 and into the second or transfer chamber 66. When the indicator element 44 of the first component 30 turns on, e.g., a green LED turns on, the clinician can stop the collection and continue to transfer the plasma portion 16 that has collected in the transfer chamber 66. For example, the next step is to transfer the plasma portion 16 to a point-of-care testing device 22.

After disconnecting the blood sampling transfer device 10 from the blood collection set 100 or other blood collection line, the blood sampling transfer device 10 may be engaged with a blood testing device 22. Next, the outlet port 60 is placed over the receiving port 24 of the point-of-care testing device 22 as shown in FIG. 5. Then, the power button 34 is depressed to advance the plasma portion 16 and to transfer the collected plasma portion 16 to the point-of-care testing device 22. The blood testing device 22 is adapted to receive the outlet port 60 of the blood sampling transfer device 10 for closed transfer of a portion of the plasma portion 16 from the blood sampling transfer device 10 to the blood testing device 22. The blood testing device 22 is adapted to receive the plasma portion 16 to analyze the blood sample and obtain test results. After that, the disposable component 50 can be removed from the first component 30, as shown in FIG. 10, and the disposable component 50 can be disposed of into a biological hazard container.

The blood sampling transfer device 10 advantageously allows for the following: a) a safe, closed system for rapidly separating a cellular portion into a clean plasma sample for transfer to a point-of-care testing device 22; b) plasma to be efficiently generated by repeatedly recirculating a cellular portion through the filter 68; c) separated plasma to be safely transferred to the point-of-care testing device 22 via a septum enabled outlet port 60; d) a system that can easily accept a cellular portion from a number of different blood collection modalities through an onboard blood inlet port 52; and e) optionally, acoustic focusing element 70 to be used to focus red blood cells in the fluidic pathway toward the center of the flow and away from the filter 68, further enhancing the efficiency of the plasma separation in the filter 68.

Some of the other advantages of the blood sampling transfer device and the blood separation and testing system of the present disclosure over prior systems are that it is a closed system which reduces blood sample exposure, it provides passive and fast mixing of the blood sample with a sample stabilizer, it facilitates separation of the blood sample without transferring the blood sample to a separate device, and it is capable of transferring pure plasma to the point-of-care testing device 22. The blood sampling transfer device of the present disclosure enables integrated blood collection and plasma creation in a closed system without centrifugation. The clinician may collect and separate the blood sample and then immediately transfer the plasma portion to the point-of-care testing device 22 without further manipulation. This enables collection and transfer of plasma to the point-of-care testing device 22 without exposure to blood. In addition, the blood sampling transfer device of the present disclosure minimizes process time by processing the blood within the blood sampling transfer device and without external machinery. Further, for tests which only require small amounts of blood, it eliminates the waste associated with blood collection and plasma separation with an evacuated tube.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A blood sampling transfer device adapted to receive a blood sample having a cellular portion and a plasma portion, the blood sampling transfer device comprising:
   a first component comprising at least two electrically driven internal miniature pumps; and
   a second component removably connected to the first component, the second component comprising:
   an inlet port,
   a flow channel,
   an outlet port, the inlet port and the outlet port in fluid communication via the flow channel,
   a filter disposed within the flow channel between the inlet port and the outlet port,
   a first chamber defined between the inlet port and the filter, and
   a transfer chamber defined between the filter and the outlet port;
   wherein the inlet port receives the blood sample upon actuation of the at least two electrically driven internal miniature pumps, and wherein the filter traps the cellular portion and allows the plasma portion to pass through the filter and into the transfer chamber; and
   wherein the at least two electrically driven internal miniature pumps are connected to one another via the first chamber to oscillate the blood sample back and forth over the filter, in which one electrically driven internal miniature pump is connected to a first side of the first chamber and another electrically driven internal miniature pump is connected to a second opposing side of the first chamber such that the filter is disposed between the one electrically driven internal miniature pump and the another electrically driven internal miniature pump.

2. The blood sampling transfer device of claim 1, wherein the first component is a reusable component.

3. The blood sampling transfer device of claim 1, wherein the second component is a disposable component.

4. The blood sampling transfer device of claim 1, wherein the filter comprises a tangential flow filter.

5. The blood sampling transfer device of claim 4, wherein the tangential flow filter utilizes a cross-flow filtration to separate the plasma portion from the cellular portion.

6. The blood sampling transfer device of claim 4, further comprising an acoustic focus element that oscillates the blood sample over the tangential flow filter in conjunction with the at least two electrically driven internal miniature pumps.

7. The blood sampling transfer device of claim 1, wherein the inlet port receives the blood sample via connection to a blood collection device.

8. The blood sampling transfer device of claim 1, wherein the outlet port is connectable to a point-of-care testing device for closed transfer of a portion of the plasma portion from the transfer chamber to the point-of-care testing device.

9. The blood sampling transfer device of claim 8, wherein with the outlet port connected to the point-of-care testing device for closed transfer, the plasma portion is transferred from the transfer chamber to the point-of-care testing device upon actuation of the at least two electrically driven internal miniature pumps.

10. The blood sampling transfer device of claim 1, comprising a power switch.

11. A blood separation and testing system for a blood sample having a cellular portion and a plasma portion, the blood separation and testing system comprising:
   a blood sampling transfer device adapted to receive the blood sample, the blood sampling transfer device comprising:
   a first component comprising at least two electrically driven internal miniature pumps, and
   a second component removably connected to the first component, the second component comprising:
   an inlet port,
   a flow channel,
   an outlet port, the inlet port and the outlet port in fluid communication via the flow channel,
   a filter disposed within the flow channel between the inlet port and the outlet port, a first chamber defined between the inlet port and the filter, and a transfer chamber defined between the filter and the outlet port, wherein the inlet port receives the blood sample upon actuation of the at least two electrically driven internal miniature pumps, and wherein the filter traps the cellular portion and allows the plasma portion to pass through the filter and into the transfer chamber, and wherein the at least two electrically driven internal miniature pumps are connected to one another via the first chamber to oscillate the blood sample back and forth over the filter, in which one electrically driven internal miniature pump is connected to a first side of the first chamber and another electrically driven internal miniature pump is connected to a second opposing side of the first chamber such that the filter is disposed between the one electrically driven internal miniature pump and the another electrically driven internal miniature pump; and a blood testing device having a receiving port connectable to the outlet port of the blood sampling transfer device for closed transfer of a portion of the plasma portion from the transfer chamber to the blood testing device.

12. The blood separation and testing system of claim 11, wherein with the outlet port connected to the blood testing device for closed transfer, the plasma portion is transferred from the transfer chamber to the blood testing device upon actuation of the at least two electrically driven internal miniature pumps.

13. The blood separation and testing system of claim 11, wherein the blood testing device comprises a point-of-care testing device.

14. The blood separation and testing system of claim 11, wherein the first component is a reusable component.

15. The blood separation and testing system of claim 11, wherein the second component is a disposable component.

16. The blood separation and testing system of claim 11, wherein the filter comprises a tangential flow filter.

17. The blood separation and testing system of claim 16, wherein the tangential flow filter utilizes a cross-flow filtration to separate the plasma portion from the cellular portion.

18. The blood separation and testing system of claim 16, further comprising an acoustic focus element that oscillates the blood sample over the tangential flow filter in conjunction with the at least two electrically driven internal miniature pumps.

19. The blood separation and testing system of claim 11, wherein the inlet port receives the blood sample via connection to a blood collection device.

20. A blood sampling transfer system adapted to receive a blood sample, the blood sampling transfer system comprising:

a reusable component comprising at least two electrically driven internal miniature pumps;

a first disposable component removably connectable to the reusable component, the first disposable component having a first inlet port, wherein the first inlet port receives the blood sample upon actuation of the at least two electrically driven internal miniature pumps; and a second disposable component removably connectable to the reusable component, the second disposable component having a second inlet port, wherein the second inlet port receives the blood sample upon actuation of the at least two electrically driven internal miniature pumps, wherein the first disposable component and the second disposable component are separated from one another and are used separately with the reusable component, and wherein the at least two internal miniature pumps are connected to the first disposable component and the second disposable component, wherein the at least two internal miniature pumps are connected to one another so as to oscillate the blood sample back and forth within, respectively, the first disposable component and the second disposable component, in which one electrically driven internal miniature pump is connected to a first side of a first chamber in the first disposable component or second disposable component and another electrically driven internal miniature pump is connected to a second opposing side of the first chamber in the first disposable component or the second disposable component with a filter disposed between the one electrically driven internal miniature pump and the another electrically driven internal miniature pump.

21. A blood sampling transfer system adapted to receive a blood sample having a cellular portion and a plasma portion, the blood sampling transfer system comprising:

a reusable component comprising at least two electrically driven internal miniature pumps;

a first disposable component removably connectable to the reusable component, the first disposable component having a first inlet port, a first flow channel, a first outlet port, the first inlet port and the first outlet port in fluid communication via the first flow channel, a first filter disposed within the first flow channel between the first inlet port and the first outlet port, a first chamber between the first inlet port and the first filter, and a first transfer chamber between the first filter and the first outlet port, wherein the first inlet port receives the blood sample upon actuation of the at least two electrically driven internal miniature pumps, wherein the first filter traps the cellular portion and allows the plasma portion to pass through the first filter and into the first transfer chamber, and wherein the at least two electrically driven internal miniature pumps are connected to one another via the first chamber to oscillate the blood sample back and forth over the first filter, in which one electrically driven internal miniature pump is connected to a first side of the first chamber and another electrically driven internal miniature pump is connected to a second opposing side of the first chamber such that the first filter is disposed between the one electrically driven internal miniature pump and the another electrically driven internal miniature pump; and a second disposable component removably connectable to the reusable component, the second disposable component having a second inlet port, a second flow channel, a second outlet port, the second inlet port and the second outlet port in fluid communication via the second flow channel, a second filter disposed within the second flow channel between the second inlet port and the second outlet port, a second chamber between the second inlet port and the second filter, and a second transfer chamber between the second filter and the second outlet port, wherein the second inlet port receives the blood sample upon actuation of the at least two electrically driven internal miniature pumps, wherein the second filter traps the cellular portion and allows the plasma portion to pass through the second filter and into the second transfer chamber, and wherein the at least two electrically driven internal miniature pumps are connected to one another via the second chamber to oscillate the blood sample back and forth over the second filter, in which one electrically driven internal miniature pump is connected to a first side of the second chamber and another electrically driven internal miniature pump is connected to a second opposing side of the second chamber such that the second filter is disposed between the one electrically driven internal miniature pump and the another electrically driven internal miniature pump, wherein the first disposable component and the second disposable component are separated from one another and are used separately with the reusable component.

\* \* \* \* \*